United States Patent [19]

Torchinsky

[11] Patent Number: 5,549,885

[45] Date of Patent: Aug. 27, 1996

[54] CHLORHEXIDINE AND GLUTARALDEHYDE MOUTHWASH

[76] Inventor: Alick Torchinsky, 1035 Champagnac, C.P. 821, St. Adele, Quebec, Canada, J0R 1L0

[21] Appl. No.: 383,013

[22] Filed: Feb. 3, 1995

[30] Foreign Application Priority Data

Feb. 15, 1994 [GB] United Kingdom .................. 9402877

[51] Int. Cl.$^6$ ................................. A61K 7/16; A61K 7/22
[52] U.S. Cl. ............................................. 424/54; 424/49
[58] Field of Search ........................................ 424/49–58

[56] References Cited

U.S. PATENT DOCUMENTS

| | | | |
|---|---|---|---|
| 3,497,590 | 2/1970 | Elgen | 424/55 |
| 4,329,333 | 5/1982 | Barr | 424/19 |
| 4,814,334 | 3/1989 | Salkin | 514/256 |
| 5,002,769 | 3/1991 | Friedman | 424/422 |

OTHER PUBLICATIONS

Food Chemical News–Apr. 30, 1984, p. 42, "Glutaraldehyde Oral Toxicity Tests indicate no Related Lesions".
Oral Manaifestations in inpatients with Aids or Aids–Related Complex, The Lancet, Aug. 2, 1986, p. 288, Barr et al.
Patients at Risk for Aids–Related Opportunistic Infections, Clinical Manifestations and Impaired Gamma Interferon Production, Murray et al, The New England Journal of Medicine, Dec. 12, 1985, pp. 1504–1510.
Candidiasis, F. Meunier, Current Topic: Review, vol. 8, No. 5, pp. 438–477.
Management of the Oral Lesions of HIV Infection, Greenspan et al, JADA, vol. 122, Aug. 1991, pp. 26–32. Aids patients should use peridex(chlorhexidine) mouth rinse twice a day.
Oral Candidiasis in High–Risk Patients as the Initial Manifestation of the Acquired Immuno–deficiency Syndrome, Klein et al, The New England Journal of Medicine, Aug. 9, 1984, pp. 354–358.
Retention of Chlorhexidine in the Human Oral Cavity, Rolla et al, Archs oral Biol., vol. 16, pp. 1109–1116. Chlorhexidine mouth rinse (antibacterial), 0.2 %.

Chlorhexidine for Prophylaxis Against Oral Infections and associated Complications in Patients receiving Bone Marrow Transplants, Ferretti et al, JADA, vol. 115, Apr. 1987, pp. 461–467. Chlorhexidine for oral candida infection.
Relationship Between Plaque–Inhibiting effect and Retention of Chlorhexidine in the Human Oral Gjermo et al, Archs oral Biol., vol. 19, pp. 1031–1034. Chlorhexidine for plaque bacteria.
An Adverse Reaction to Glutaraldehyde, Jul. 9, 1983, The Medical Journal of Australia, p. 14.
Contact Dermatitis from Glutaraldehyde, Jordan et al, Arch Derm/vol. 105, Jan. 1972, pp. 94–95.
Glutaraldehyde and Calcium Hydroxide, A pulp Dressing Material, Hanna, Mar. 21, 1992, Brit. Dent. J., 1972, 227–231.
Localized Epidermolysis Bullosa, Report of Two Cases and Evaluation of Therapy with Glutaraldehyde, DesGroseilliers et al, Arch Dermato/vol. 109, Jan. 1974, pp. 70–72.
Abstract No. 813, Acute Toxicity and Irritancy of Glutaraldehyde, Ballantyne et al, Toxicologist 1985, 4, 204.
A Critical Review of the Toxicology of Glutaraldehyde, Beauchamp Jr. et al, Critical Reviews in Toxicology, 22(3, 4):143–174 (1992). Glutaraldehyde used in dentistry (p. 149).
On the Specific Molecular Configuration of Neurotoxic Aliphatic Hexacarbon Compounds Causing Central Peripheral Distal Axonopathy, Spencer et al, Biology and Applied Pharmacology, 44, 17–28 (1978).

*Primary Examiner*—Shep K. Rose
*Attorney, Agent, or Firm*—Swabey Ogilvy Renault

[57] ABSTRACT

A pharmaceutical composition contains chlorhexidine and glutaraldehyde in a pharmaceutically acceptable carrier; in the form of a mouthwash, the composition is effective in controlling fungal or yeast infections in the oral cavity, such as associated with subjects suffering from AIDS, cancer and periodontal diseases; in particular the composition is effective against fungi of the genus *Candida* including *Candida albicans* and *Candida krusei*.

16 Claims, No Drawings

CHLORHEXIDINE AND GLUTARALDEHYDE MOUTHWASH

BACKGROUND OF THE INVENTION

1. Field of the Invention

This invention relates to a pharmaceutical composition and a method of treatment; more especially the invention is concerned with such a composition in the form of a mouthwash for treatment of fungal or yeast infections in the oral cavity; and with a method of treating subjects with fungal or yeast infections.

2. Description of Prior Art

Fungal or yeast infections in the mouth and throat are exhibited by patients suffering from AIDS, cancer and periodontal disorders.

There is no satisfactory treatment for these infections.

Chlorhexidine or N,N'-bis(4-chlorophenyl)- 3,12-diimino-2,4,11,13-tetraazatetradecanediimidamide is a known disinfectant and topical antibacterial.

Glutaraldehyde or 1,3-diformylpropane is a known disinfectant used in high level disinfection of surgical equipment including equipment which can not be heat sterilized.

SUMMARY OF THE INVENTION

It is an object of this invention to provide a pharmaceutical composition, more especially a composition in the form of a mouthwash.

It is a further object of this invention to provide such a composition for treatment of *Candida* infections, especially in subjects having AIDS, cancer or periodontal diseases.

It is a further object of this invention to provide a method of treating subjects having fungal or yeast infections.

It has now been found that a pharmaceutical composition based on chlorhexidine and glutaraldehyde is effective in controlling such fungal and yeast infections and provides superior results when compared with prior compositions.

In accordance with the invention there is provide a pharmaceutical composition comprising a pharmacologically effective, pharmacologically acceptable amount of chlorhexidine and a pharmacologically effective, pharmacologically acceptable amount of glutaraldehyde, in association with a pharmaceutically acceptable carrier.

In another aspect of the invention there is provided a method of treating subjects having fungal or yeast infections which comprises application to the site of the infection, of a composition of the invention.

In accordance with still another aspect of the invention there is provided use of a composition of the invention in the treatment of subjects having AIDS, cancer or periodontal diseases.

DESCRIPTION OF PREFERRED EMBODIMENTS

The composition of the invention is, in particular, an antifungal or antiyeast infection composition.

The composition of the invention is especially useful as a mouthwash, in which the pharmaceutically acceptable carrier is water.

Employed as a mouthwash the composition may suitably contain about 0.2%, by volume, of the chlorhexidine and about 0.004%, by volume, of the glutaraldehyde.

In general the composition should not contain more than 0.5%, by volume, of the chlorhexidine; and not more than about 0.01%, by volume, of gluteraldehyde.

The composition may also suitably contain a lower alcohol of 1 to 4 carbon atoms, especially ethyl alcohol, which has antiseptic activity. The alcohol may be present in an amount of about 7%, by volume.

In order to render the composition more palatable as a mouthwash it may suitably include a flavouring agent and a colourant, in a flavouring or colouring amount, respectively. Suitable flavouring agents include anise oil and peppermint oil, each of which may be present in an amount of about 0.06%, by volume; suitable colourants include Red Dye No. 7 which may be employed in an amount of about 0.001%, by volume.

In the case in which anise oil or peppermint oil are included in the composition it is appropriate to include a dispersing, suspending or emulsifying agent to disperse, suspend or emulsify the oils in the aqueous medium; one suitable agent is a derivative of castor oil and ethylene oxide also described as a polyethylene glycol glycerol hydrogenated castor oil available from BASF under the Trade Mark Cremophor; this agent may be used in an amount of about 0.8%, by volume.

The composition of the invention in the form of a mouthwash is found to be effective in controlling fungus or yeast infections of the genus *Candida,* for example, *Candida albicans* and *Candida krusei*. These infections are experienced by persons suffering from AIDS and cancer and also by persons suffering from periodontal diseases. The composition does not provide a cure for the infection, but the infection may be controlled by periodic use of the composition. Typically the mouthwash may be applied by gargling or rinsing the mouth with the mouthwash 2–3 times. Surprisingly, the mouthwash is found to be non-toxic to mucous tissue in the oral cavity.

Chlorhexidine and glutaraldehyde are both soluble in water, and can be readily dissolved in an aqueous pharmaceutically acceptable carrier. However, when flavouring oils, such as anise oil and peppermint oil are employed, the oils are first mixed with the alcohol and the suspending agent. Separately the chlorhexidine and the glutaraldehyde are mixed with a first portion of the water to form a solution; and the colourant is mixed with a second portion of the water.

The mix of oils and alcohol is admixed with the aqueous solution of chlorhexidine and glutaraldehyde until a homogeneous suspension is obtained; thereafter the aqueous solution of the colourant is admixed with the suspension, and the resulting suspension is filtered.

It will be understood that the % amounts indicated herein for individual ingredients are in wt. % Furthermore, these amounts are not intended to be restrictive, but are merely illustrative of useful amounts. It is well within the skill of persons in the art to determine useful variations in the amounts by routine experiments.

In comparison studies a composition of the invention was compared with Virkon, an oxidizing disinfectant based on potassium monoperoxysulphate manufactured by Antec International Ltd. of Suffolk, England; the composition of the invention was of the following formulation:

| | |
|---|---|
| Chlorhexidine | 50 ml (1%) = 0.2% (20% solution) |
| Glutaraldehyde | 2 ml (0.2%) = 0.004% (2% solution) |
| Cremophor | 8 g (0.8%) |

| | |
|---|---|
| Red Dye No. 7 | 0.01 mg (0.001%) |
| Anise oil | 0.6 ml (0.06%) |
| Peppermint oil | 0.6 ml (0.06%) |
| Alcohol 95% | 70 ml (7%) |
| Water | 1000 ml |

Both compositions were found to be effective in killing *Candida albicans* within seconds. In the case of *Candida krusei* it took 20 minutes for the Virkon to destroy the yeast, which is clearly too long an exposure time for a mouthwash; on the other hand, the composition of the invention killed the strain instantly by cell lysis.

I claim:

1. A pharmaceutical liquid mouthwash composition comprising, as active pharmacological agents, a pharmacologically effective, pharmacologically acceptable amount of chlorhexidine and a pharmacologically effective, pharmacologically acceptable amount of glutaraldehyde, in association with a pharmaceutically acceptable carrier.

2. A composition according to claim 1, wherein said carrier is water.

3. A composition according to claim 2, further including a lower alcohol of 1 to 4 carbon atoms.

4. A composition according to claim 3, wherein said alcohol is ethyl alcohol.

5. A composition according to claim 2, further including flavouring and colouring additives.

6. A composition according to claim 5, including a suspending agent.

7. A method of treating a subject with a fungal or yeast infection comprising oral application to an oral site of the infection of a liquid mouthwash composition comprising, as active pharmacological agents, a pharmacologically effective, pharmacologically acceptable amount of chlorhexidine and a pharmacologically acceptable amount of glutaraldehyde.

8. A method according to claim 7, in which said infection is a *Candida* infection.

9. A method according to claim 8, in which said application is to the mouth of the subject.

10. A method according to claim 7, in which said subject is a patient having AIDS, cancer or a periodontal disease.

11. A method according to claim 8, wherein said infection is *Candida albicans* or *Candida krusei*.

12. An antifungal, antiyeast infection oral mouthwash liquid composition comprising, as active pharmacological agents, a pharmacologically effective, pharmacologically acceptable amount of chlorhexidine and a pharmacologically effective pharmacologically acceptable amount of glutaraldehyde, together with a flavouring amount of a flavouring agent in an aqueous vehicle.

13. A composition according to claim 12, further including a colouring amount of a colourant.

14. A composition according to claim 13, which contains not more than 0.5%, by volume of said chlorhexidine and not more than about 0.01%, by volume of glutaraldehyde.

15. A composition according to claim 14, in which said flavouring agent is anise oil or peppermint oil and further including a dispersing agent effective to disperse said oil in said aqueous vehicle.

16. A composition according to claim 15, wherein said dispersing agent is a polyethylene glycol glycerol hydrogenated castor oil.

* * * * *